(12) United States Patent  
Senn-Bilfinger

(10) Patent No.: US 6,503,923 B1
(45) Date of Patent: Jan. 7, 2003

(54) HALOALKOXY IMIDAZONAPHTHYRIDINES

(75) Inventor: Jörg Senn-Bilfinger, Constance (DE)

(73) Assignee: ALTANA Pharma AG, Constance (DE)

( * ) Notice: Subject to any disclaimer, the term of this patent is extended or adjusted under 35 U.S.C. 154(b) by 0 days.

(21) Appl. No.: 09/926,267

(22) PCT Filed: Apr. 14, 2000

(86) PCT No.: PCT/EP00/03388

§ 371 (c)(1),
(2), (4) Date: Oct. 3, 2001

(87) PCT Pub. No.: WO00/63211

PCT Pub. Date: Oct. 26, 2000

(30) Foreign Application Priority Data

Apr. 17, 1999 (EP) .............................. 99107688

(51) Int. Cl.[7] ................. A61K 31/4375; C07D 471/14; A61P 1/04
(52) U.S. Cl. ......................... 514/293; 546/82
(58) Field of Search ............................ 546/82; 514/293

(56) References Cited

U.S. PATENT DOCUMENTS 4,468,400 A    8/1984   Gold et al. ................. 424/256

FOREIGN PATENT DOCUMENTS

| WO | 94/18199 | 8/1994 |
|---|---|---|
| WO | 98/42707 | 10/1998 |
| WO | 00/17200 | 3/2000 |

*Primary Examiner*—Evelyn Mei Huang
(74) *Attorney, Agent, or Firm*—Jacobson Holman PLLC

(57) ABSTRACT

Compounds of formula I

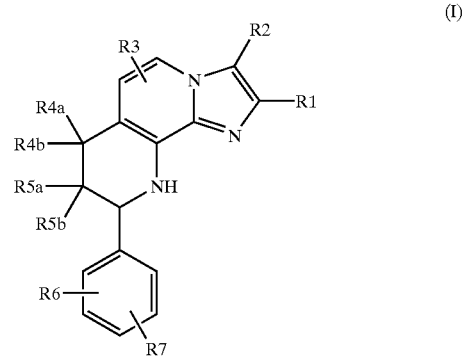

in which R1, R2, R3, R4a, R4b, R5a, R5b, R6 and R7 have the meanings indicated in the specification, and their pharmacologically tolerable salts are useful for preventing and/or treating gastrointestinal diseases.

19 Claims, No Drawings

HALOALKOXY IMIDAZONAPHTHYRIDINES

This is a nationalization of PCT/EP00/03388 filed Apr. 14, 2000 and published in English.

FIELD OF APPLICATION OF THE INVENTION

The invention relates to novel compounds which are used in the pharmaceutical industry as active compounds for the production of medicaments.

KNOWN TECHNICAL BACKGROUND

U.S. Pat. No. 4,468,400 describes tricyclic imidazo[1,2-a]pyridines having various ring systems fused to the imidazopyridine parent structure, which are intended to be suitable for the treatment of peptic ulcers.—International Patent Application WO98/42707 discloses tetrahydroimidazonaphthyridines having a very specific substitution pattern, which are likewise intended to be suitable for the treatment of gastric and intestinal disorders.

DESCRIPTION OF THE INVENTION

The invention relates to compounds of the formula I

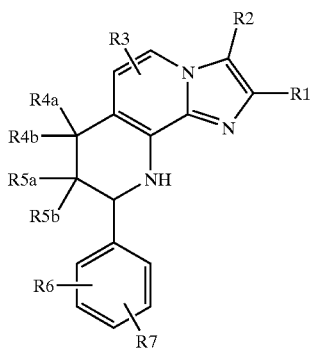

(I)

in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3 is hydrogen, halogen, trifluoromethyl, 1–4C-alkyl, 2–4C-alkenyl or 2–4C-alkynyl,
one of the substituents R4a and R4b is hydrogen and the other is hydrogen, hydroxyl, 1–4C-alkoxy, 1–4C-alkoxy-1–4C-alkoxy, 1–4C-alkylcarbonyloxy or the radical R4', or in which R4a and R4b together are O (oxygen),
where R4' is 1–4C-alkoxy which is completely or mainly substituted by halogen,
one of the substituents R5a and R5b is hydrogen and the other is hydrogen, hydroxyl, 1–4C-alkoxy, 1–4C-alkoxy-1–4C-alkoxy, 1–4C-alkylcarbonyloxy or the radical R5', or in which R5a and R5b together are O (oxygen),
where R5' is 1–4C-alkoxy which is completely or mainly substituted by halogen,
where one of the substituents R4a and R4b must have the meaning R4' and/or one of the substituents R5a and R5b must have the meaning R5',
or in which
one of the substituents R4a and R4b on the one hand and one of the substituents R5a and R5b on the other hand in each case is hydrogen, and the other substituents in each case together form a 1–2C-alkylenedioxy radical which is completely or partially substituted by halogen,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl and
R7 is hydrogen, halogen, 1–4C-alkyl or 1–4C-alkoxy,
and their salts.

1–4C-alkyl represents strain-chain or branched alkyl radicals having 1 to 4 carbon atoms. Examples which may be mentioned are the butyl, isobutyl, sec-butyl, tert-butyl, propyl, isopropyl, ethyl and methyl radical.

Hydroxy-1–4C-alkyl represents abovementioned 1–4C-alkyl radicals which are substituted by a hydroxyl group. Examples which may be mentioned are the hydroxymethyl, the 2-hydroxyethyl and the 3-hydroxypropyl radical.

Halogen within the meaning of the invention is bromine, chlorine or fluorine.

2–4C-alkenyl represents straight-chain or branched alkenyl radicals having 2 to 4 carbon atoms. Examples which may be mentioned are the 2-butenyl, 3-butenyl, 1-propenyl and the 2-propenyl radical (allyl radical).

2–4C-alkynyl represents straight-chain or branched alkynyl radicals having 2 to 4 carbon atoms. Examples which may be mentioned are the 2-butynyl, 3-butynyl and preferably the 2-propynyl radical (propargyl radical).

1–4C-alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radical.

1–4C-alkoxy-1–4C-alkoxy represents one of the abovementioned 1–4C-alkoxy radicals which is substituted by a further 1–4C-alkoxy radical. Examples which may be mentioned are the radicals 2-methoxyethoxy (CH$_3$—O—CH$_2$—CH$_2$—O—) and 2-ethoxyethoxy (CH$_3$—CH$_2$—O—CH$_2$—CH$_2$—O—).

1–4C-alkylcarbonyl represents a radical which, in addition to the carbonyl group, contains one of the abovementioned 1–4C-alkyl radicals. An example which may be mentioned is the acetyl radical.

1–4C-alkylcarbonyloxy represents a 1–4C-alkylcarbonyl group which is bonded to an oxygen atom. An example which may be mentioned is the acetoxy radical (CH$_3$CO—O—).

Completely or mainly halogen-substituted 1–4C-alkoxy which may be primarily mentioned are chlorine and/or, in particular, fluorine-substituted 1–4C-alkoxy radicals. Examples of halogen-substituted 1–4C-alkoxy which may be mentioned are the 2,2,2-trichloroethoxy, the hexachloroisopropoxy, the pentachloroisopropoxy, the 1,1,1-trichloro-3,3,3-trifluoro-2-propoxy, the 1,1,1-trichloro-2-methyl-2-propoxy, the 1,1,1-trichloro-2-propoxy, the 3-bromo-1,1,1-trifluoro-2-propoxy, the 3-bromo-1,1,1-trifluoro-2-butoxy, the 4-bromo-3,3,4,4-tetrafluoro-1-butoxy, the chlorodifluoromethoxy, the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radical.

Completely or partially halogen-substituted 1–2C-alkylenedioxy which may be mentioned in particular are fluorine-substituted 1–2C-alkylenedioxy, for example the difluoroethylenedioxy (—O—CF$_2$—CH$_2$—O—), the tetrafluoroethylenedioxy (—O—CF$_2$—CF$_2$—O—) and in particular the difluoromethylenedioxy (—O—CF$_2$—O—), and the 1,1,2-trifluoroethylenedioxy radical (—O—CF$_2$CHF—O—) and also the chlorotrifluoroethylenedioxy radical.

1–4C-alkoxycarbonyl represents a carbonyl group to which one of the abovementioned 1–4C-alkoxy radicals is bonded. Examples which may be mentioned are the methoxycarbonyl (CH$_3$O—C(O)—) and the ethoxycarbonyl radical (CH$_3$CH$_2$O—C(O)—).

1–4C-alkoxycarbonylamino represents an amino radical which is substituted by one of the abovementioned 1–4C-alkoxycarbonyl radicals. Examples which may be mentioned are the ethoxycarbonylamino and the methoxycarbonylamino radical.

1–4C-alkoxy-1–4C-alkoxycarbonyl represents a carbonyl group to which one of the abovementioned 1–4C-alkoxy-1–4C-alkoxy radicals is bonded. Examples which may be mentioned are the 2-methoxyethoxycarbonyl(CH$_3$—O—CH$_2$CH$_2$—O—CO—) and the 2-ethoxyethoxycarbonyl radical (CH$_3$CH$_2$—O—CH$_2$CH$_2$—O—CO—).

1–4C-alkoxy-1–4C-alkoxycarbonylamino represents an amino radical which is substituted by one of the abovementioned 1–4C-alkoxy-1–4C-alkoxycarbonyl radicals. Examples which may be mentioned are the 2-methoxyethoxycarbonylamino and der 2-ethoxyethoxycarbonylamino radical.

Possible salts of compounds of the formula I—depending on substitution—are especially all acid addition salts. Particular mention may be made of the pharmacologically tolerable salts of the inorganic and organic acids customarily used in pharmacy. Those which are suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether it is a mono- or polybasic acid and depending on which salt is desired—in an equimolar quantitative ratio or one differing therefrom.

Pharmacologically intolerable salts, which can be initially obtained, for example, as process products in the preparation of the compounds according to the invention on the industrial scale, are converted into pharmacologically tolerable salts by processes known to the person skilled in the art.

It is known to the person skilled in the art that the compounds according to the invention and their salts can contain various amounts of solvents if they are isolated, for example, in crystalline form. The invention therefore also comprises all solvates and in particular all hydrates of the compounds of the formula I, and all solvates and in particular all hydrates of the salts of the compounds of the formula I.

The compounds of the formula I have at least two chiral centers. The invention relates to all conceivable stereoisomers in any desired mixing ratio to one another, including the pure enantiomers, which are a preferred subject of the invention.

An exemplary preferred radical R1 is the methyl radical.

Exemplary preferred radicals R2 are the methyl and the hydroxymethyl radical.

R3 in the context of the present invention is preferably hydrogen.

Compounds worthy of mention are those of the formula I, in which

R1 is 1–4C-alkyl,

R2 is 1–4C-alkyl or hydroxy-1–4C-alkyl,

R3 is hydrogen, one of the substituents R4a and R4b is hydrogen and the other is hydrogen, hydroxyl, 1–4C-alkoxy, 1–4C-alkoxy-1–4C-alkoxy or the radical R4', where R4' is completely or mainly halogen-substituted halogen-substituted 1–4C-alkoxy, one of the substituents R5a and R5b is hydrogen and the other is hydrogen, hydroxyl, 1–4C-alkoxy, 1–4C-alkoxy-1–4C-alkoxy or the radical R5', where R5' is completely or mainly halogen-substituted 1–4C-alkoxy, where one of the substituents R4a and R4b must have the meaning R4' and/or one of the substituents R5a and R5b must have the meaning R5', or in which one of the substituents R4a and R4b on the one hand and one of the substituents R5a and R5b on the other hand is in each case hydrogen, and the other substituents in each case together form a completely or partially halogen-substituted 1–2C-alkylenedioxy radical, R6 is hydrogen, halogen or trifluoromethyl and R7 is hydrogen or halogen, and their salts.

Compounds of the invention to be emphasized are those of the formula I*

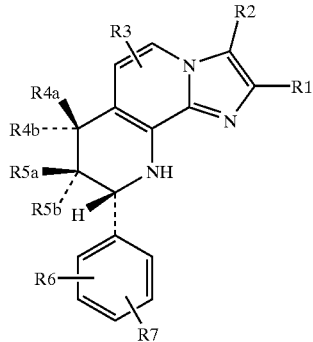

(I*)

in which

R1 is 1–4C-alkyl,

R2 is 1–4C-alkyl or hydroxy-1–4C-alkyl,

R3 is hydrogen, one of the substituents R4a and R4b is hydrogen and the other is hydrogen, hydroxyl, 1–4C-alkoxy, 1–4C-alkoxy-1–4C-alkoxy or the radical R4', where R4' is completely or mainly fluorine-substituted 1–4C-alkoxy or chlorodifluoromethoxy, one of the substituents R5a and R5b is hydrogen and the other is hydrogen, hydroxyl, 1–4C-alkoxy, 1–4C-alkoxy-1–4C-alkoxy or the radical R5', where R5' is completely or mainly fluorine-substituted 1–4C-alkoxy or chlorodifluoromethoxy, where one of the substituents R4a and R4b must have the meaning R4' and/or one of the substituents R5a and R5b must have the meaning R5', or in which one of the substituents R4a and R4b on the one hand and one of the substituents R5a and R5b on the other hand is in each case hydrogen, and the other substituents in each case together form a completely or partially fluorine-substituted 1–2C-alkylenedioxy radical or chlorotrifluoroethylenedioxy radical, R6 is hydrogen, halogen or trifluoromethyl and R7 is hydrogen or halogen, and their salts.

An embodiment (embodiment a) of the compounds of the formula I* to be emphasized is that in which one of the substituents R4a and R4b is hydrogen and the other is the radical R4' and one of the substituents R5a and R5b is hydrogen and the other is hydroxyl.

A further embodiment (embodiment b) of the compounds of the formula I* to be emphasized is that in which one of the substituents R4a and R4b is hydrogen and the other is the radical R4' and one of the substituents R5a and R5b is hydrogen and the other is 1–4C-alkoxy or 1–4C-alkoxy-1–4C-alkoxy.

A further embodiment (embodiment c) of the compounds of the formula I* to be emphasized is that in which one of the substituents R4a and R4b is hydrogen and the other is the radical R4' and one of the substituents R5a and R5b is hydrogen and the other is the radical R5'.

A further embodiment (embodiment d) of the compounds of the formula I* to be emphasized is that in which one of the substituents R4a and R4b is hydrogen and the other is 1–4C-alkoxy or 1–4C-alkoxy-1–4C-alkoxy and one of the substituents R5a and R5b is hydrogen and the other is the radical R5'.

Compounds I* of embodiments a, b, c and d particularly to be emphasized are those in which R1 is 1–4C-alkyl, R2 is 1–4C-alkyl, R3 is hydrogen, R4' is completely or mainly fluorine-substituted 1–4C-alkoxy or chlorodifluoromethoxy, R5' is completely or mainly fluorine-substituted 1–4C-alkoxy or chlorodifluoromethoxy, R6 is hydrogen and R7 is hydrogen, and their salts.

Preferred compounds I* of embodiment a are those in which

R1 is 1–4C-alkyl,

R2 is 1–4C-alkyl,

R3 is hydrogen, one of the substituents R4a and R4b is hydrogen and the other is R4', where R4' is completely or mainly fluorine-substituted 1–4C-alkoxy or chlorodifluoromethoxy, one of the substituents R5a and R5b is hydrogen and the other is hydroxyl, R6 is hydrogen and R7 is hydrogen, and their salts.

Preferred compounds I* of embodiment b are those in which

R1 is 1–4C-alkyl,

R2 is 1–4C-alkyl,

R3 is hydrogen, one of the substituents R4a and R4b is hydrogen and the other is R4', where R4' is completely or mainly fluorine-substituted 1–4C-alkoxy or chlorodifluoromethoxy, one of the substituents R5a and R5b is hydrogen and the other is 1–4C-alkoxy or 1–4C-alkoxy-1–4C-alkoxy, R6 is hydrogen and R7 is hydrogen, and their salts.

Preferred compounds I* of embodiment c are those in which

R1 is 1–4C-alkyl,

R2 is 1–4C-alkyl,

R3 is hydrogen, one of the substituents R4a and R4b is hydrogen and the other is R4', where R4' is completely or mainly fluorine-substituted 1–4C-alkoxy or chlorodifluoromethoxy, one of the substituents R5a and R5b is hydrogen and the other is R5', where R5' is completely or mainly fluorine-substituted 1–4C-alkoxy or chlorodifluoromethoxy, R6 is hydrogen and R7 is hydrogen, and their salts.

Preferred compounds I* of embodiment d are those in which

R1 is 1–4C-alkyl,

R2 is 1-C-alkyl,

R3 is hydrogen, one of the substituents R4a and R4b is hydrogen and the other is 1–4C-alkoxy or 1–4C-alkoxy-1–4C-alkoxy, one of the substituents R5a and R5b is hydrogen and the other is R5', where R5' is completely or mainly fluorine-substituted 1–4C-alkoxy or chlorodifluoromethoxy, R6 is hydrogen and R7 is hydrogen, and their salts.

Selected preferred compounds I* are those of embodiments a, b, c and d in which R5b is hydrogen.

Selected particularly preferred compounds I* are those of embodiments a, b, c and d in which R5b is hydrogen and R4a is hydrogen.

Selected preferred radicals R4' and R5' are the 2,2,2-trifluoroethoxy- and the difluoromethoxy radical.

The following exemplary selected preferred compounds according to the invention may be explicitly mentioned with the aid of formula I** below with the substituent meanings for R4a, R4b and R5a in the following Table 1 (Tab. 1):

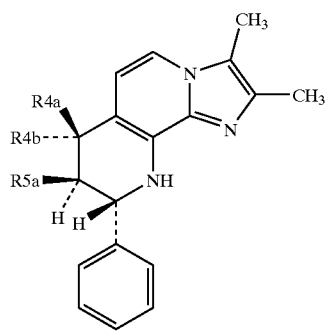

TABLE 1

| R4a | R4b | R5a |
|---|---|---|
| H | —OCF₃ | —OH |
| H | —OCF₂CHF₂ | —OH |
| H | —OCH₂CF₃ | —OH |
| H | —OCClF₂ | —OH |
| H | —OCHF₂ | —OH |
| —OCF₃ | H | —OH |
| —OCF₂CHF₂ | H | —OH |
| —OCH₂CF₃ | H | —OH |
| —OCClF₂ | H | —OH |
| —OCHF₂ | H | —OH |
| H | —OCF₃ | —OCH₃ |
| H | —OCF₂CHF₂ | —OCH₃ |
| H | —OCH₂CF₃ | —OCH₃ |
| H | —OCClF₂ | —OCH₃ |
| H | —OCHF₂ | —OCH₃ |
| H | —OCF₃ | —OCH₂CH₂OCH₃ |
| H | —OCF₂CHF₂ | —OCH₂CH₂OCH₃ |
| H | —OCH₂CF₃ | —OCH₂CH₂OCH₃ |
| H | —OCClF₂ | —OCH₂CH₂OCH₃ |
| H | —OCHF₂ | —OCH₂CH₂OCH₃ |
| —OCF₃ | H | —OCH₃ |
| —OCF₂CHF₂ | H | —OCH₃ |
| —OCH₂CF₃ | H | —OCH₃ |
| —OCClF₂ | H | —OCH₃ |
| —OCHF₂ | H | —OCH₃ |
| —OCF₃ | H | —OCH₂CH₂OCH₃ |
| —OCF₂CHF₂ | H | —OCH₂CH₂OCH₃ |
| —OCH₂CF₃ | H | —OCH₂CH₂OCH₃ |
| —OCClF₂ | H | —OCH₂CH₂OCH₃ |
| —OCHF₂ | H | —OCH₂CH₂OCH₃ |
| —OCF₃ | H | —OCF₃ |
| —OCF₂CHF₂ | H | —OCF₂CHF₂ |
| —OCH₂CF₃ | H | —OCH₂CF₃ |
| —OCClF₂ | H | —OCClF₂ |
| —OCHF₂ | H | —OCHF₂ |
| H | —OCF₃ | —OCF₃ |
| H | —OCF₂CHF₂ | —OCF₂CHF₂ |
| H | —OCH₂CF₃ | —OCH₂CF₃ |
| H | —OCClF₂ | —OCClF₂ |
| H | —OCHF₂ | —OCHF₂ |
| H | —OCH₃ | —OCF₃ |
| H | —OCH₃ | —OCF₂CHF₂ |
| H | —OCH₃ | —OCH₂CF₃ |
| H | —OCH₃ | —OCClF₂ |
| H | —OCH₃ | —OCHF₂ |
| H | —OCH₂CH₂OCH₃ | —OCF₃ |
| H | —OCH₂CH₂OCH₃ | —OCF₂CHF₂ |
| H | —OCH₂CH₂OCH₃ | —OCH₂CF₃ |
| H | —OCH₂CH₂OCH₃ | —OCClF₂ |
| H | —OCH₂CH₂OCH₃ | —OCHF₂ |
| —OCH₃ | H | —OCF₃ |
| —OCH₃ | H | —OCF₂CHF₂ |
| —OCH₃ | H | —OCH₂CF₃ |
| —OCH₃ | H | —OCClF₂ |
| —OCH₃ | H | —OCHF₂ |
| —OCH₂CH₂OCH₃ | H | —OCF₃ |
| —OCH₂CH₂OCH₃ | H | —OCF₂CHF₂ |
| —OCH₂CH₂CCH₃ | H | —OCH₂CF₃ |
| —OCH₂CH₂OCH₃ | H | —OCClF₂ |
| —OCH₂CH₂OCH₃ | H | —OCHF₂ |

The compounds according to the invention are prepared, for example, starting from the compounds of the formula I disclosed in WO98/42707, in which at least one of the substituents R4a, R4b, R5a and R5b has the meaning hydroxyl (subsequently called "starting compounds"). Starting from these starting compounds, the preparation of the compounds according to the invention—depending on which final product is desired—can be carried out in various ways, for example by acid-catalyzed etherification of the starting compounds with compounds of the formula R4'-H or R5'-H, for example as described below.

The substances according to the invention are isolated and purified in a manner known per se, for example by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid, or to which the desired acid is then added. The salts are obtained by filtering, reprecipitating, precipitating with a nonsolvent for the addition salt or by evaporation of the solvent. Salts obtained can be converted into the free compounds, which in turn can be converted into salts, by alkalization or by acidification. In this way, pharmacologically nontolerable salts can be converted into pharmacologically tolerable salts.

The pure enantiomers, in particular the pure enantiomers of the formula I*, which are a preferred subject of the invention, can be obtained in a manner familiar to the person skilled in the art, for example by enantioselective synthesis, by chromatographic resolution on chiral separating columns, by derivatization with chiral auxiliary reagents, subsequent separation of diastereomers and cleavage of the chiral auxiliary group, by salt formation with chiral acids, subsequent resolution of the salts and liberation of the desired compound from the salt, or by (fractional) crystallization from a suitable solvent.

The following examples illustrate the invention in greater detail, without restricting it. The compounds according to the invention can be prepared in an analogous manner to that described in the examples. The abbreviation RT stands for room temperature, h stands for hour(s), min for minute(s), m.p. for melting point and dec. for decomposition.

EXAMPLES 1. (7R, 8R, 9R)-2,3-Dimethyl-8-hydroxy-7-(2,2,2-trifluoroethoxy)-9-phenyl-7,8,9,10-tetrahydroimidazo[1,2-h][1,7]naphthyridine 4 g of (7R, 8R, 9R)-2,3-dimethyl-7,8-dihydroxy-9-phenyl-7,8,9,10-tetrahydroimidazo[1,2-h][1,7] naphthyridine are dissolved in 40 ml of 2,2,2-trifluoroethanol and treated dropwise with 1.5 g of conc. sulfuric acid. After stirring at RT for 15 min, the mixture is poured onto 60 ml of ice water. 0.6 g of solid sodium hydroxide is added and the mixture is extracted three times with 40 ml of dichloromethane each time at pH=7.5. The collected organic extracts are combined and washed with a little water. After stripping off the solvent in vacuo, the residual viscous oil is purified on silica gel (ethylacetate/methanol=20:1). 2.8 g of diastereomer mixture of the title compound are obtained (about 20% 7-R, about 80% 7-S). 200 mg of this mixture are purified on silica gel (thick layer chromatography, petroleum ether/triethylamine=1:1). 20 mg of the title compound of m.p. 178–180° C. are obtained.

2. (7S, 8R, 9R)-2,3-Dimethyl-8-hydroxy-7-(2,2,2-trifluoroethoxy)-9-phenyl-7,8,9,10-tetrahydrolmidazo[1,2-h][1,7]naphthyridine 20 mg of the title compound of m.p. 158–160° C. are obtained analogously to Example 1 after purification twice on silica gel.

Commercial Utility

The compounds of the formula I and their salts have valuable pharmacological properties which make them commercially utilizable. In particular, they exhibit a marked inhibition of the secretion of gastric acid and an excellent gastric and intestinal protective action in warm-blooded mammals, in particular humans. The compounds according to the invention are distinguished here by a high selectivity of action, an advantageous duration of action, a particularly good enteral activity, the absence of significant side effects and a wide therapeutic breadth.

"Gastric and intestinal protection" is understood in this connection as meaning the prevention and treatment of gastrointestinal diseases, in particular gastrointestinal inflammatory diseases and lesions (such as, for example, stomach ulcer, duodenal ulcer, gastritis, functional gastropathy due to hyperacidity or medicaments), which can be caused, for example by microorganisms (e.g. Helicobacter pylori), bacterial toxins, medicaments (e.g. certain antiinflammatories and antirheumatics), chemicals, e.g. ethanol), gastric acid or stress situations.

The compounds according to the invention surprisingly prove to be clearly superior to the compounds known from the prior art in their excellent properties in various models in which the antiulcerogenic and the antisecretory properties are determined. On account of these properties, the compounds of the formula I and their pharmacologically tolerable salts are outstandingly suitable for use in human and veterinary medicine, where they are used, in particular, for the treatment and/or prophylaxis of disorders of the stomach and/or intestine.

A further subject of the invention is therefore the compounds according to the invention for use in the treatment and/or prophylaxis of the abovementioned diseases.

The invention likewise comprises the use of the compounds according to the invention for the production of medicaments which are employed for the treatment and/or prophylaxis of the abovementioned diseases.

The invention furthermore comprises the use of the compounds according to the invention for the treatment and/or prophylaxis of the abovementioned diseases.

A further subject of the invention is medicaments which contain one or more compounds of the formula I and/or their pharmacologically tolerable salts.

The medicaments are prepared by methods which are known per se and familiar to the person skilled in the art. As medicaments, the pharmacologically active compounds (=active compounds) according to the invention are either employed as such, or preferably in combination with suitable pharmaceutical excipients or vehicles in the form of tablets, coated tablets, capsules, suppositories, patches (e.g. as TTSs), emulsions, suspensions or solutions, where the active compound content can advantageously be between 0.1 and 95% and where by the appropriate choice of the excipient and vehicles a pharmaceutical administration form (e.g. a sustained-release form or an enteric-coated form) exactly tailored to the active compound and/or to the desired onset of action can be achieved.

The person skilled in the art is familiar on the basis of his/her expert knowledge with excipients and vehicles which are suitable for the desired pharmaceutical formulations. In addition to solvents, gelforming agents, suppository bases, tablet excipients and other active compound vehicles, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of a number, preferably 1 to 4, of individual doses to achieve the desired result. In the case of parenteral treatment, similar or (in particular in the case of intravenous administration of the active compounds), as a rule, lower doses can be used. Any person skilled in the art can fix the optimum dose and type of administration necessary in each case on the basis of his/her expert knowledge.

If the compounds according to the invention and/or their salts are to be employed for the treatment of the abovementioned diseases, the pharmaceutical preparation can also contain one or more pharmacologically active constituents of other pharmaceutical groups. Examples which may be mentioned are: tranquilizers (for example from the benzodiazepines group, e.g. diazepam), spasmolytics (e.g. bietamiverine or camylofine), anticholinergics (e.g. oxyphencyclimine or phencarbamide), local anesthetics (e.g. tetracaine or procaine), if appropriate also enzymes, vitamins or amino acids.

In particular to be emphasized in this connection is the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or furthermore with so-called peripheral antcholinergics (e.g. pirenzepine, telenzepine) and also with gastrin antagonists with the aim of increasing the main action in an additive or superadditive sense and/or eliminating or decreasing the side effects, or furthermore the combination with antibacterially active substances (e.g., for example, cephalosporins, tetracyclines, penicillins, macrolides, nitroimidazoles or otherwise bismuth salts) for the control of *Helicobacter pylori*. Antibacterially active combination partners which can be mentioned are, for example, meziocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (e.g. clarithromycin+metronidazole).

Pharmacology

The excellent gastric protective action and the gastric and antisecretory action of the compounds according to the invention can be demonstrated in investigations in animal experimental models. The compounds according to the invention investigated in the model mentioned below have been provided with numbers which correspond to the numbers of these compounds in the examples.

Testing of the Antisecretory Action in Perfused Rat Stomachs

The influence of the compounds according to the invention after intravenous administration on the pentagastrin-stimulated acid secretion of perfused rat stomachs in vivo is shown in Table A which follows.

TABLE A

| No. | Dose ($\mu$mol/kg) i.v. | Inhibition of acid secretion (%) |
|---|---|---|
| 1 | 3 | 100 |

Methodology

The abdomen of anesthetized rates (CD rat, female, 200–250 g; 1.5 g/kg i.m. urethane) was opened after tracheotomy by means of a median upper abdominal incision and a PVC catheter was fixed transorally in the esophagus and another via the pylorus such that the ends of the tubes just projected into the gastric lumen. The catheter leading from the pylorus led outwards into the right abdominal wall through a side opening.

After thorough rinsing (about 50–100 ml), warm physiological NcCl solution (37° C.) was continuously passed through the stomach (0.5 ml/min, pH 6.8–6.9, Braun-Unita I). The pH (pH meter 632, glass electrode EA 147; $\phi$=5 mm, Metrohm) and, by titration with a freshly prepared 0.01 N NaOH solution to pH 7 (dosimat 665 Metrohm), the secreted HCl were determined in the effluent, in each case collected at an interval of 15 minutes.

The gastric secretion was stimulated by continuous infusion of 1 pg/kg (=1.65 ml/h) of i.v. pentagastrin (left femoral vein) about 30 min after the end of the operation (i.e. after determination of 2 preliminary fractions). The substances to be tested were administered intravenously in 1 ml/kg of liquid volume 60 min after the start of the continuous pentagastrin infusion.

The body temperature of the animals was kept at a constant 37.8–38° C. by infrared irradiation and heat pads (automatic, stepless control by means of a rectal temperature sensor).

What is claimed is:

1. A compound of the formula I

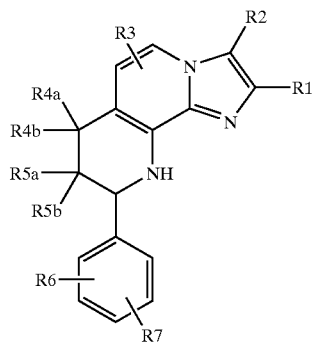

(I)

in which
R1 is hydrogen, 1–4C-alkyl or hydroxy-1–4C-alkyl,
R2 is hydrogen, 1–4C-alkyl, hydroxy-1–4C-alkyl, halogen, 2–4C-alkenyl or 2–4C-alkynyl,
R3 is hydrogen, halogen, trifluoromethyl, 1–4C-alkyl, 2–4C-alkenyl or 2–4C-alkynyl,
one of the substituents R4a and R4b is hydrogen and the other is hydrogen, hydroxyl, 1–4C-alkoxy, 1–4C-alkoxy-1–4C-alkoxy, 1–4C-alkylcarbonyloxy or the radical R4', or in which R4a and R4b together are O (oxygen),
  where R4' is 1–4C-alkoxy which is completely or mainly substituted by halogen,
one of the substituents R5a and R5b is hydrogen and the other is hydrogen, hydroxy 1–4C-alkoxy, 1–4C-alkoxy-1–4-C-alkoxy, 1–4-C-alkylcarbonyloxy or the radical R5', or in which R5a and R5b together are O (oxygen),
  where R5' is 1–4C-alkoxy which is completely or mainly substituted by halogen,
where one of the substituents R4a and R4b must have the meaning R4' and/or one of the substituents R5a and R5b must have the meaning R5',
or in which
  one of the substituents R4a and R4b on the one hand and one of the substituents R5a and R5b on the other hand in each case is hydrogen, and the other substituents in each case together form a 1–2C-alkylenedioxy radical which is completely or partially substituted by halogen,
R6 is hydrogen, halogen, 1–4C-alkyl, 1–4C-alkoxy, 1–4C-alkoxycarbonylamino, 1–4C-alkoxy-1–4C-alkoxycarbonylamino or trifluoromethyl and
R7 is hydrogen, halogen, 1–4C-alkyl or 1–4C-alkoxy,
or a salt thereof.

2. A compound as claimed in claim 1, which has the formula I*

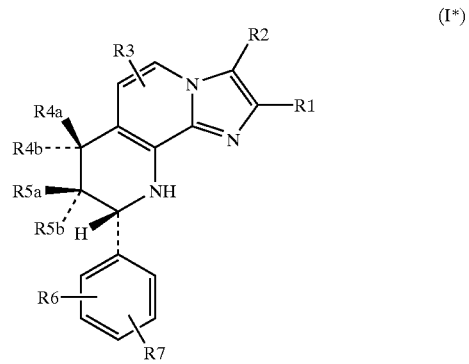

(I*)

in which
R1 is 1–4C-alkyl,
R2 is 1–4C-alkyl or hydroxy-1–4C-alkyl,
R3 is hydrogen,
one of the substituents R4a and R4b is hydrogen and the other is hydrogen, hydroxyl, 1–4C-alkoxy, 1–4C-alkoxy-1–4C-alkoxy or the radical R4',
  where
  R4' is completely or mainly fluorine-substituted 1–4C-alkoxy or chlorodifluoromethoxy,
one of the substituents R5a and R5b is hydrogen and the other is hydrogen, hydroxyl, 1–4C-alkoxy, 1–4C-alkoxy-1–4C-alkoxy or the radical R5', where
R5' is completely or mainly fluorine-substituted 1–4C-alkoxy or chlorodifluoromethoxy,
where one of the substituents R4a and R4b must have the meaning R4' and/or one of the substituents
R5a and R5b must have the meaning R5',
or in which
one of the substituents R4a and R4b on the one hand and one of the substituents R5a and R5b on the other hand is in each case hydrogen, and the other substituents in each case together form a completely or partially fluorine-substituted 1–2C-alkylenedioxy radical or chlorotrifluoroethylenedioxy radical,
R6 is hydrogen, halogen or trifluoromethyl and
R7 is hydrogen or halogen,
or a salt thereof.

3. A compound as claimed in claim 2, in which
R1 is 1–4C-alkyl,
R2 is 1–4C-alkyl,
R3 is hydrogen,
one of the substituents R4a and R4b is hydrogen and the other is R4',
where
R4' is completely or mainly fluorine-substituted 1–4C-alkoxy or chlorodifluoromethoxy,
one of the substituents R5a and R5b is hydrogen and the other is hydroxyl,
R6 is hydrogen and
R7 is hydrogen,
or a salt thereof.

4. A compound as claimed in claim 2, in which
R1 is 1–4C-alkyl,
R2 is 1–4C-alkyl,
R3 is hydrogen,
one of the substituents R4a and R4b is hydrogen and the other is R4',
where
R4' is completely or mainly fluorine-substituted 1–4C-alkoxy or chlorodifluoromethoxy,
one of the substituents R5a and R5b is hydrogen and the other is 1–4C-alkoxy or 1–4C-alkoxy-1–4C-alkoxy,
R6 is hydrogen and
R7 is hydrogen,
or a salt thereof.

5. A compound as claimed in claim 2, in which
R1 is 1–4C-alkyl,
R2 is 1–4C-alkyl,
R3 is hydrogen,
one of the substituents R4a and R4b is hydrogen and the other is R4',
where
R4' is completely or mainly fluorine-substituted 1–4C-alkoxy or chlorodifluoromethoxy,
one of the substituents R5a and R5b is hydrogen and the other is R5',
where
R5' is completely or mainly fluorine-substituted 1–4C-alkoxy or chlorodifluoromethoxy,
R6 is hydrogen and
R7 is hydrogen,
or a salt thereof.

6. A compound as claimed in claim 2, in which
R1 is 1–4C-alkyl,
R2 is 1–4C-alkyl,
R3 is hydrogen,
one of the substituents R4a and R4b is hydrogen and the other is 1–4C-alkoxy or 1–4C-alkoxy-1–4C-alkoxy,
one of the substituents R5a and R5b is hydrogen and the other is R5',
where
R5' is completely or mainly fluorine-substituted 1–4C-alkoxy or chlorodifluoromethoxy,
R6 is hydrogen and
R7 is hydrogen,
or a salt thereof.

7. A compound 1* as claimed in claim 2 in which R5b is hydrogen.

8. A compound 1* as claimed in claim 7 wherein R4a is hydrogen.

9. A compound 1* as claimed in claim 3 wherein R5b is hydrogen.

10. A compound 1* as claimed in claim 9 wherein R4a is hydrogen.

11. A compound 1* as claimed in claim 4 wherein R5b is hydrogen.

12. A compound 1* as claimed in claim 11 wherein R4a is hydrogen.

13. A compound 1* as claimed in claim 5 wherein R5b is hydrogen.

14. A compound 1* as claimed in claim 13 wherein R4a is hydrogen.

15. A compound 1* as claimed in claim 6 wherein R5b is hydrogen.

16. A compound 1* as claimed in claim 15 wherein R4a is hydrogen.

17. A pharmaceutical composition comprising a compound as claimed in claim 1 and/or a pharmacologically tolerable salt thereof together with a customary pharmaceutical excipient and/or vehicle.

18. A method of preparing a pharmaceutical composition by combining an active ingredient for preventing or treating a gastrointestinal disease with a customary pharmaceutical excipient and/or vehicle, wherein the active ingredient is a compound as claimed in claim 1 or a pharmacologically tolerable salt thereof.

19. A method for preventing or treating an amenable gastrointestinal disease which comprises administering to a subject prone to or afflicted with such disease an effective amount of a compound as claimed in claim 1 or a pharmacologically tolerable salt thereof.

* * * * *